United States Patent [19]

Lovinger et al.

[11] Patent Number: 4,528,273
[45] Date of Patent: Jul. 9, 1985

[54] MICROORGANISM STRAINS FOR THE FERMENTATIVE PREPARATION OF L-SERINE

[75] Inventors: Gerald G. Lovinger, Gaithersburg; Susan A. Whitehead, Columbia, both of Md.

[73] Assignee: W. R. Grace & Co., New York, N.Y.

[21] Appl. No.: 554,452

[22] Filed: Nov. 22, 1983

[51] Int. Cl.$^3$ .......................... C12P 13/06; C12R 1/15
[52] U.S. Cl. ..................................... 435/116; 435/843
[58] Field of Search ................................ 435/116, 843

[56] References Cited
PUBLICATIONS

Morinaga et al.–Chem. Abst., vol. 93 (1980) p. 43927v.
Ajinomoto–Chem. Abst., vol. 94 (1981) p. 45608m.

Primary Examiner—Sam Rosen
Attorney, Agent, or Firm—Jill H. Krafte

[57] ABSTRACT

A method for improving a strain of microorganisms capable of converting glycine to L-serine by selecting for strain-improving mutations such that the improved strain is serine dehydratase negative and is resistant to at least one of the amino acid analogs serine hydroxamate, glycine hydroxamate or methionine hydroxamate.

17 Claims, No Drawings

MICROORGANISM STRAINS FOR THE FERMENTATIVE PREPARATION OF L-SERINE

BACKGROUND OF THE INVENTION

This invention relates to a process for producing the amino acid L-serine from glycine by microbial fermentation. More particularly, it relates to the strain improvement of an L-serine producing microorganism in order to produce commercial quantities of L-serine in less time and with a minimum of contaminating amino acids.

L-serine is a non-essential amino acid which is used primarily as a dietary supplement in parenteral nutrition. Commercial production of L-serine is by fermentation of certain microorganisms which produce and accumulate L-serine in the fermentation broth. For example, U.S. Pat. No. 4,183,786 (Nakayama et al.) discloses a process for converting glycine to L-serine by use of an aqueous medium containing glycine and microbial cells of a mutant belonging to *Nocardia butanica*. Similarly, it is known from U.S. Pat. No. 3,623,952 (Kubota et al.) that L-serine may be accumulated by culturing certain strains of *Arthrobacter citreus*, *Brevibacterium helvolum*, *Corynebacterium sp.* and *Candida pulcherrima* on conventional media containing glycine. Additionally, U.S. Pat. No. 3,880,741 (Kageyama et al.) discloses that artificially induced mutants of *Corynebacterium glycinophilum* which require leucine, isoleucine, methionine, tryptophan, serine or glycine for their growth will produce L-serine from glycine in higher yields than the parent strain which does not require such nutrients.

Glycine is a costly precursor and is difficult to separate from L-serine. For these reasons, considerable research efforts have been made to improve the rate and efficiency of the bioconversion, thereby increasing L-serine product yields and decreasing levels of unconverted glycine remaining after fermentation.

SUMMARY OF THE INVENTION

Use of the process disclosed herein for improving L-serine producing microorganisms results in fermentations characterized by enhanced reaction rates and conversion efficiency as well as increased product yields. These results are based on improvement of the parent microorganism strains by inducing mutations which leave the microorganisms serine dehydratase negative and resistant to at least one of three amino acid analogs, serine hydroxamate, methionine hydroxamate or glycine hydroxamate.

It is a primary object of this invention to provide an efficient and economical process for the microbial production of L-serine.

A related object is to reduce the quantities of unconverted glycine present in the broth at the conclusion of the fermentation by improving the efficiency of the bioconversion of glycine to L-serine.

A similarly related object is to increase industrial productivity and efficiency by reducing the fermentation period required to achieve maximum accumulation of L-serine in the broth.

To achieve these basic objectives, this invention seeks to improve microorganism strains which are known to convert glycine to L-serine by introducing sequential chemical and natural mutations to achieve the desired improvements.

Another object is to provide a microbial process for the bioconversion of glycine to L-serine which does not also result in the production of significant amounts of contaminating amino acids.

Moreover, it is desired to induce strain improvements which decrease the tendency of the microorganisms to degrade L-serine.

DETAILED DESCRIPTION OF THE INVENTION

Fermentation of certain microorganisms in a medium containing glycine results in accumulation of L-serine in the fermentation broth. The bioconversion of glycine to L-serine involves the aldol condensation of glycine and a one-carbon unit by the enzyme serine hydroxymethyltransferase (E.C. 2.1.2.1). The one-carbon unit may be present in the medium or may be formed enzymatically by the microorganism. The cofactors utilized in the aldol condensation are tetrahydrofolate and pyridoxal-5-phosphate.

In order to achieve maximum yields of L-serine, the process disclosed herein utilizes microorganisms in which the controls on L-serine production have been deregulated by inducing resistance to at least one of three amino acid analogs. Additionally, the L-serine degradation pathway involving serine dehydratase has been at least partially inactivated in the microorganisms of this invention. Each of these aspects has been shown to improve the reaction rate, efficiency and/or yield in the bioconversion of glycine to L-serine.

A strain of *Corynebacterium glycinophilum* (also known as *Corynebacterium sp.*) known to produce L-serine and identified as ATCC 21341 was obtained from the American Type Culture Collection, 12301 Parklawn Drive, Rockville, Md. 20852. Fermentation of this strain in shake flasks for 6 days resulted in production levels of 1.5 to 2.0 grams/liter of L-serine. By means of the strain improvement sequence disclosed herein, L-serine production was increased fourfold, to yields of about 8.0 or more grams/liter and the fermentation period was shortened to about 4 or 5 days. The following discussion and Examples are in terms of the improvement of *Corynebacterium glycinophilum*, but the strain improvement procedure disclosed may be useful with other L-serine producing microorganisms to achieve improved rates, yields and/or reaction efficiency in the conversion of glycine to L-serine.

As one aspect of this invention, mutations are induced which result in decreased degradation of the L-serine end-product by the microorganisms. This degradation of L-serine significantly undermines the potential product yields in a commercial fermentation process. By the method disclosed herein, mutants may be produced which make minimal internal use of L-serine so that most, if not all, of the L-serine produced during the fermentation remains in the fermentation broth and is available for collection and separation.

As another aspect of this invention, suitable microorganism strains are improved by deregulating the metabolic controls on the production of L-serine from glycine. This deregulation results from the induction of mutations which confer on the microorganism resistance to high levels of the hydroxamate derivatives of serine, methionine and glycine. In the strain improvement process disclosed herein, not all analogs of L-serine have been found to be effective in increasing fermentation yields of L-serine. It has been discovered that resistance to the three listed compounds is particularly effective in this process.

It also has been found that the combination of these traits in a single strain will improve product yields considerably. That is, mutants may be produced which both have a decreased capacity to degrade L-serine and are resistant to high levels of methionine hydroxamate, serine hydroxamate and/or glycine hydroxamate. It is preferred that the mutant be resistant to each of these three analogs.

These strain improvements are achieved by putting the selected microorganism strain through a protocol of chemical and spontaneous mutations in which various means of selective pressure are applied to result in a strain with the desired characteristics. Mutagens which may be utilized in this invention include ultraviolet light or any chemical mutagen. Broad spectrum mutagens, such as ultraviolet light and N-methyl-N'-nitro-N-nitrosoguanidine ("NG"), create large numbers of lesions and therefore will have a broad and significant effect on the characteristics of the mutant. However, since the genetic damage is widespread, these mutagens also have a greater tendency to cause deleterious changes. Site specific mutagens, such as ethylmethane sulfonate ("EMS"), create relatively more controlled mutations as well as mutations of a specific type, depending on the mutagen. The dosage or exposure levels of the particular mutagen selected will be determined by reference to conventional practice.

The preferred embodiment, described in detail below, makes use of a particular sequence of mutations to create the improved microorganism strain. First, a broad spectrum mutagen (NG) is used for selection of a serine dehydratase negative mutant strain. It is believed that the lesions produced by exposure to NG may predispose the mutant strains to later mutations confering analog resistance. Next, mutants which also are resistant to the three hydroxamate derivatives are selected, either using a site specific mutagen such as EMS or by relying on spontaneous mutation. This sequence is believed to be the most advantageous in creating a viable strain with the desired characteristics. In alternative embodiments, however, it may be desired to use an altered selection sequence. In particular, an altered sequence may be desired for induction of the hydroxamate analog resistances. It also may be desired to use the somewhat less powerful site specific mutagens throughout the protocol.

As a first step in the preferred protocol, a parent strain is selected which is known to convert glycine to L-serine. For example, any of the microorganisms disclosed in the Nakaymama et al. and Kubota et al. patents discussed in the Background section above may be suitable. The selection of the parent strain is within the knowledge of one skilled in this art.

To select for a mutation which leaves the microorganism serine dehydratase negative, the following preferred method is employed. A healthy culture of the parent strain is obtained and exposed to the mutagen NG. Microorganisms from this culture are plated onto a rich medium, i.e., one which provides a complete array of nutrients, and incubated at conventional temperatures for about 2 to about 5 days. Individual colonies are picked from this medium onto plates of "minimal" and "complete" media in order to select colonies which do not degrade L-serine to provide a source of nitrogen. The minimal medium contains sufficient nutrients to support growth of the microorganisms. In the complete medium, the nitrogen source is replaced with L-serine.

After incubating on these plates for a period sufficient to determine growth or lack of growth, about 1 to about 7 days, clones are selected which grew on the minimal medium but not on the complete medium. These clones exhibit serine dehydratase negativity, that is, they are unable to degrade L-serine for use as a nitrogen source. Clones will begin to appear in the early part of the growth period. However, since not all the serine dehydratase negative clones will be L-serine producing strains as well, it is preferred to incubate the plates for at least several days in order to create a larger pool of clones from which L-serine overproducers may be selected. The highest L-serine producing clones are selected for the next cycle of mutation and selection.

To establish resistance to methionine hydroxamate, a mutagen-exposed cell population is incubated on a solid growth medium containing methionine hydroxamate in sufficient quantities to inhibit the growth of non-resistant microorganisms. Suitable quantities of methionine hydroxamate will be about 0.1 to about 1.0 mg per milliliter of growth medium. Analog resistance may be achieved either by spontaneous mutation or by exposing the organism to a chemical mutagen or ultraviolet light prior to plating on the analog-containing medium. The plates, after incubation for about 3 to 7 days at conventional temperatures, will exhibit colonies which are methionine hydroxamate resistant.

In the preferred embodiment, these colonies should be serine dehydratase negative as well. To detemine whether this latter characteristic has been retained, it may be desired to re-plate the colonies on the minimal and complete media as described above. As before, the serine dehydratase negative colonies will grow on the minimal but not on the complete medium.

To establish resistance to serine hydroxamate and glycine hydroxamate, the same general procedures are used as to establish resistance to methionine hydroxamate. For serine hydroxamate resistance, suitable levels of serine hydroxamate will be about 0.1 to about 1.0 mg/ml. However, it appears that microorganisms display a higher sensitivity to glycine hydroxamate. Therefore, it may be desired to use lower concentrations of glycine hydroxamate in the medium to ensure the survival of an adequate number of clones. For example, levels of about 0.01 to about 0.8 mg/ml may be used.

As can be seen, the mutation protocol of this invention involves serially selecting mutants of the parent strain which exhibit the desired characteristics, that is, mutants which are serine dehydratase negative and are resistant to at least one of the amino acid analogs serine hydroxamate, glycine hydroxamate or methionine hydroxamate. By "serially selecting," it is meant that the mutant strain obtained at each step of the protocol is used in the succeeding step. That is, the induced mutations are intended to be cumulative. For example, in the preferred embodiment described above, the serial selection of mutants is as follows:

Step 1: The parent strain was exposed to the mutagen NG and serine dehydratase negative mutants selected.

Step 2: The mutants obtained by the procedures of Step 1 were exposed to EMS and grown on methionine hydroxamate-containing medium and mutants resistant to methionine hydroxamate were selected.

Step 3: The mutants obtained by the procedures of Step 2 were grown on serine hydroxamate-containing medium and mutants resistant to serine hydroxamate were selected.

Step 4: The mutants obtained by the procedures in Step 3 were grown on glycine hydroxamate-containing medium and mutants resistant to glycine hydroxamate were selected.

By following this serial selection protocol, mutant strains were obtained which were serine dehydratase negative and which also were resistant to all three amino acid analogs (methionine hydroxamate, serine hydroxamate and glycine hydroxamate).

Once strains with the desired characteristics are obtained, they may be tested in shake flasks or fermentors for L-serine production. In this way, one or more improved strains may be selected which exhibit the desired characteristic(s): the largest product yields, maximal levels of product in the shortest fermentation period and/or display the best conversion efficiency (i.e., result in the least residual unconverted glycine).

This test fermentation may be by conventional methods. The culture medium may be any fermentation medium containing a carbon source, nitrogen source, inorganic salts and, where desired, other minor organic nutrients. As the carbon source, fermentable sugars, protein hydrolyzates and proteins may be used. As the nitrogen source, urea, ammonium salts of organic acids (e.g., ammonium acetate or ammonium oxalate) and ammonium salts of inorganic acids (e.g., ammonium sulfate, ammonium nitrate or ammonium chloride) may be satisfactory. The amounts of the carbon and nitrogen sources in the medium are from 0.001 to 20 w/v percent. Inorganic elements (e.g., potassium phosphate or magnesium sulfate) and/or vitamins (e.g., biotin or thiamine) may be added as well.

Conventional fermentation temperatures are between about 20° C. and about 45° C., preferably about 26° C. to about 34° C., depending on the microorganism. The pH range is about 5 to 8, preferably about 6.5 to about 7.5. The fermentation is accomplished in about 16 to 176 hours, typically 96 hours at the flask-level, during which time L-serine accumulates in the fermentation broth. Cells and other solid culture components may be removed from the broth by conventional procedures such as filtration or centrifugation.

At the completion of the fermentation, or at any time during the fermentation period, L-serine titers may be determined by high pressure liquid chromatography (HPLC) or by any convenient method. Glycine levels may also be determined. From the results of these analyses, the clone(s) with the desired characteristics may be identified.

When selecting a microorganism for laboratory, pilot plant or industrial fermentation, L-serine production can be enhanced substantially by selecting an improved strain with the characteristics described above. The methods described above for the test fermentations and those described in the Examples which follow will provide useful guidelines for producing L-serine with the improved microorganisms of this invention. Mutant strains of *Corynebacterium glycinophilum* have been identified as having the preferred characteristics: decreased capacity to degrade L-serine and resistance to serine hydroxamate, glycine hydroxamate and methionine hydroxamate. Two of these mutants have been irrevocably deposited with the American Type Culture Collection, 12301 Parklawn Drive, Rockville, Md. 30852, without restriction as to availability and are identified as ATCC 39495 and ATCC 39496. As indicated earlier, the process of this invention may be used to improve other L-serine producing strains in the same manner.

The Examples which follow are given for illustrative purposes only and are not meant to limit the invention described herein. The following abbreviations have been used throughout in describing the invention:

°C.—degrees Centigrade
EMS—ethylmethane sulfonate
gm—grams(s)
HPLC—high pressure liquid chromatography
l—liter(s)
M—molar
mg—milligram(s)
ml—milliliter(s)
NG—N-methyl-N'-nitro-N-nitrosoguanidine
RPM—rotations per minute
%—percent The culture media used in the Examples were prepared as indicated below.

A. Nitrosoguanidine Mutation Medium

| | |
|---|---|
| Glucose | 0.5% |
| Peptone | 1.0% |
| Meat extract | 1.0% |
| NaCl | 0.5% |
| Yeast extract | 0.5% |
| Agar | 2.0% |
| De-ionized Water | 94.5% |

The listed ingredients were heated to boiling and then were steam sterilized at 121° C. for 15 minutes. The sterile mixture was poured into petri dishes and allowed to set.

B. Serine Seed Medium

| | |
|---|---|
| Glucose | 3.00% |
| $(NH_4)_2SO_4$ | 0.30% |
| $K_2HPO_4$ | 0.16% |
| $KH_2PO_4$ | 0.04% |
| $MgSO_4.7H_2O$ | 0.05% |
| Yeast extract | 0.50% |
| Peptone | 2.00% |
| De-ionized Water | 93.95% |

The listed ingredients were mixed and the medium was autoclaved at 121° C. for 20 minutes.

C. Luria Broth

| | |
|---|---|
| Bacto-Tryptone (Difco) | 10.0 gm |
| Bacto-Yeast extract (Difco) | 5.0 gm |
| NaCl | 10.0 gm |
| 1.0 M NaOH | 1.5 ml |

The ingreients were combined in one liter de-ionized water and were steam sterilized at 121° C. for 15 minutes.

D. Serine Production Medium

| | |
|---|---|
| Glucose | 50.00 gm/l |
| $(NH_4)_2SO_4$ | 2.00 gm/l |
| $NH_4NO_3$ | 3.00 gm/l |
| $KH_2PO_4$ | 1.00 gm/l |
| $MgSO_4.7H_2O$ | 0.50 gm/l |
| Glycine | 20.00 gm/l |
| L-glutamic acid | 0.50 gm/l |

| | |
|---|---|
| L-methionine | 0.50 gm/l |
| L-valine | 0.50 gm/l |
| CaCO4 | 25.00 gm/l |
| Biotin | 0.20 mg/l |
| Thiamine-HCl | 1.00 mg/l |
| Riboflavin | 2.00 mg/l |
| Folic acid | 1.00 mg/l |
| Calcium pantothenate | 1.00 mg/l |
| Nicotinamide | 1.00 mg/l |
| Pyroxidine | 1.00 mg/l |
| Pyridoxal | 0.20 mg/l |
| PABA | 1.00 mg/l |

The first nine listed ingredients were mixed in the indicated quantities per liter de-ionized water and autoclaved at 112° C. for 12 minutes. The CaCO3 was autoclaved separately at 112° C. for 12 minutes. The remaining ingredients were mixed, filter sterilized and added to the cooled medium, along with the CaCO3.

E. Modified Serine Production Medium

This was prepared in the same manner as the Serine Production Medium, except that 3.0% glucose is used rather than 5.0% glucose.

F. Serine Production Minimal Medium

| | |
|---|---|
| Glucose | 0.500% |
| (NH4)2SO4 | 0.200% |
| KH2PO4 | 0.150% |
| K2HPO4 | 0.050% |
| MgSO4.7H2O | 0.050% |
| NaCl | 0.010% |
| FeSO4.7H2O | 0.001% |
| MnSO4.4H2O | 0.001% |
| CaCl2.2H2O | 0.001% |
| Biotin | 100 μg/l |
| Thiamine-HCl | 1.0 mg/l |
| Agar | 2.000% |

The ingredients were heated to boiling in one liter de-ionized water and autoclaved at 121° C. for 15 minutes. The mixture was poured into petri dishes and allowed to set.

G. Serine Production Complete Medium

This was prepared in the same manner as the Serine Production Minimal Medium, except that 0.2% L-serine was substituted for 0.2% (NH4)2SO4.

EXAMPLE I

A loopful of *Corynebacterium glycinophilum* (a.k.a *Corynebacterium sp.*) ATCC 21341 was inoculated from a refrigerated Nutrient Agar (Difco) slant into 5.0 ml of Luria Broth in a 20 ml test tube. The tube was incubated at 32° C. for 24 hours. The cells were centrifuged, washed with and resuspended in 10 ml of 0.1M sodium phosphate buffer (pH 7.0) in a test tube.

N-methyl-N'-nitro-N-nitrosoguanidine ("NG") was added to the suspended cells to achieve a concentration of 0.5 mg/ml. The NG-cell-buffer mixture was held at room temperature for 30 minutes. The cells then were washed with 10 ml buffer, centrifuged and rewashed with buffer five more times. The washed cells were resuspended in 5.0 ml of the buffer. Next, 100 μl aliquots of the suspended cells were spread onto plates of Nitrosoguanidine Mutation Medium. The plates were incubated at 30° C. for two days.

Individual colonies were picked from these plates onto plates of Serine Production Minimal Medium and Serine Production Complete Medium to test for the ability of each colony to use L-serine as a nitrogen source. A clone, designated SWSER-1, was identified which grew on the Minimal but not the Complete Medium. This clone contained a mutation which lead to its decreased ability to degrade L-serine.

The SWSER-1 clone was grown in 5.0 ml of Serine Seed Medium for 2 days at 30° C. and 260 RPM. A 2.0 ml aliquot was transferred to 50 ml Serine Production Medium in a 250 ml nonindented Erlenmeyer flask and grown for 5 days at 30° C. and 125 RPM. This procedure was duplicated, using the parent microorganism strain ATCC 21341. At the end of this period, samples of the fermentation broth from each strain were assayed by HPLC. Clone SWSER-1 had produced 4.4 mg/ml L-serine and the parent ATCC 21341 had produced 1.6 mg/ml L-serine.

EXAMPLE II

A fresh Nutrient Agar slant of clone SWSER-1 was washed with 10 ml 0.1M potassium phosphate buffer (pH 7.0) and the resulting suspension was placed in a 20 ml sterile Corning (TM) centrifuge tube. Ethylmethane sulfonate ("EMS") was added to the suspension to a concentration of 0.06M EMS in the cell suspension. The suspension was vortexed to mix the cells with the mutagen and then incubated at 30° C. for 18 hours.

After incubation, the cells were centrifuged, washed twice with 10 ml 0.1M potassium phosphate buffer and resuspended in 10 ml buffer. With each washing, the cells were transferred to clean tubes in order to eliminate any mutagen clinging to the test tube walls. The washed cell suspension was spread in 100 μl aliquots onto plates of Nutrient Agar containing 0.5 mg/ml of the amino acid analog methionine hydroxamate. These plates were incubated at 30° C. for 5 days. Colonies which grew on the plates containing methionine hydroxamate had the desired mutation(s) conferring resistance to that analog.

One of these colonies, designated SWSER-1-23 was selected for L-serine production. It was grown for 24 hours in 5.0 ml Serine Seed Medium at 30° C., 260 RPM. Aliquots of 2.0 ml then were transferred to 250 ml nonindented Erlenmeyer flasks containing 50 ml Serine Production Medium and were incubated for 6 days at 30° C., 125 RPM. This procedure was duplicated using the SWSER-1 clone. By HPLC analysis, the fermentation broth of SWSER-1-23 was found to contain 4.8 mg/ml L-serine and the broth of SWSER-1 contained 3.3 mg/ml L-serine.

EXAMPLE III

A Nutrient Agar slant of Clone SWSER-1-23, the strain obtained in Example III, was washed with and resuspended in 10 ml 0.1M potassium phosphate buffer (pH 7.0). The suspension, in 100 μl aliquots, was spread onto plates of Nutrient Agar containing 0.5 mg/ml serine hydroxamate. The plates were incubated at 30° C. for 5 days. At the end of the incubation period, there was significant growth on the plate, indicating that the SWSER-1-23 clone contained a mutation which caused it to be resistant to serine hydroxamate.

EXAMPLE IV

A Nutrient Agar slant of clone SWSER-1-23, the strain obtained in Example III, was washed with 10 ml de-ionized water. Next, 100 μl aliquots of the cell suspension were spread onto plates of Serine Production Minimal Medium which contained 0.5 mg/ml glycine hydroxamate. The plates were incubated for 5 days at 30° C. At the end of the incubation period, the colonies growing on the plate represented strains which had undergone spontaneous mutation leaving them resistant to glycine hydroxamate.

Two of these colonies, designated SWSER-1-23-18 (now ATCC 39495) and SWSER-1-23-20 (now ATCC 39496) were grown overnight in 5.0 ml Serine Seed Medium at 31° C. The cultures then were placed in 50 ml Serine Production Medium and incubated for 6 days at 31° C., 300 RPM. This procedure was duplicated using the SWSER-1-23 clone. By HPLC analysis, the fermentation broth of SWSER-1-23-18 (ATCC No. 39495) was found to contain 4.8 mg/ml L-serine, the broth of SWSER-1-23-20 (ATCC 39496) contained 5.2 mg/ml L-serine and the broth of SWSER-1-23 contained 2.7 mg/ml L-serine.

EXAMPLE V

A Nutrient Agar slant of clone SWSER-1-23-20 (ATCC 39496) was washed with 10.0 ml 0.1M potassium phosphate buffer (pH 7.0). Aliquots of 2.5 ml of the resulting cell suspension were placed in 250 ml nonindented Erlenmeyer flasks containing 50 ml of Serine Seed Medium. The flasks were incubated overnight at 31° C., 260 RPM. Next, 2.0 ml of the seed culture was inoculated into 50 ml of Modified Serine Production Medium in a 250 ml nonindented Erlenmeyer flask. The flask was incubated for 5 days at 31° C., 260 RPM, with addition of 1% glucose at 48 and at 72 hours. HPLC analysis revealed a titer of 8.8 mg/ml L-serine at the end of the 5 day fermentation period.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method for improving a strain of *Corynebacterium glycinophilum* capable of converting glycine to L-serine which comprises introducing mutations into the strain which cause the microorganisms to exhibit as characteristics: (1) serine dehydratase negativity and (2) resistance to at least one of the amino acid analogs (a) serine hydroxamate, (b) glycine hydroxamate or (c) methionine hydroxamate.

2. The method of claim 1 in which the chosen characteristics are provided by serially selecting, in any order, mutants of a parent strain, Selections being made from the group consisting of:

A. selecting a mutant characterized by serine dehydratase negativity,
B. selecting a mutant characterized by serine hydroxamate resistance,
C. selecting a mutant characterized by glycine hydroxamate resistance, and
D. selecting a mutant characterized by methionine hydroxamate resistance, provided that Selection A must be chosen as one of the serial selections.

3. The method of claim 2 in which at least one of the mutations is induced by exposure to one of the chemical mutagens ethylmethane sulfonate or N-methyl-N'-nitro-N-nitrosoguanidine.

4. The method of claim 2 in which Selection A comprises:

(a) picking colonies onto a plate of minimal medium,
(b) picking the colonies onto a plate of medium identical to that of step (a) except that it contains L-serine in place of the nitrogen source,
(c) incubating the plates of steps (a) and (b) at about 20° to 45° C. for about 1 to about 7 days, and
(d) selecting colonies which grew on the plate of step (a) but not on the plate of step (b).

5. The method of claim 2 in which Selection B comprises:

(a) plating cells onto a solid growth medium comprising about 0.1 to 1.0 mg/ml of serine hydroxamate,
(b) incubating the plate of step (a) at about 20° to 45° C. for about 1 to about 7 days, and
(c) selecting colonies which grew on said plate.

6. The method of claim 2 in which Selection C comprises:

(a) plating cells onto a solid growth medium comprising about 0.01 to 0.8 mg/ml of glycine hydroxamate,
(b) incubating the plate of step (a) at about 20° to 45° C. for about 1 to 7 days, and
(c) selecting colonies which grew on said plate.

7. The method of claim 2 in which Selection D comprises:

(a) plating cells onto a solid growth medium comprising about 0.1 to about 1.0 mg/ml of methionine hydroxamate,
(b) incubating the plate of step (a) at about 20° to 45° C. for about 1 to about 7 days, and
(c) selecting colonies which grew on said plate.

8. The method of claim 2 in which all four Selections A, B, C and D are made.

9. The method of claim 8 in which Selection A is chosen as the first serial selection and N-methyl-N'-nitro-N-nitrosoguanidine is the mutagen used in making Selection A.

10. A process for preparing L-serine by fermentation which comprises culturing under aerobic conditions an improved strain of *Corynebacterium glycinophilum*, a microorganism capable of converting glycine to L-serine, said improved strain characterized by (1) serine dehydratase negativity and (2) resistance to at least one of the amino acid analogs serine hydroxamate, glycine hydroxamate or methionine hydroxamate.

11. The process of claim 10 in which L-serine accumulated in said medium during the fermentation is recovered from the medium.

12. The process of claim 10 in which the fermentation is carried out at a temperature of from 20° to 45° C. and a pH of about 5 to about 8 for about 16 to 176 hours.

13. The process of claim 10 in which said improved strain has the identifying characteristics of ATCC No. 39495 or ATCC No. 39496.

14. An improved strain of *Corynebacterium glycinophilum*, an L-serine producing microorganism, said strain being characterized by (1) serine dehydratase negativity and (2) resistance to at least one of the amino acid analogs serine hydroxamate, glycine hydroxamate or methionine hydroxamate.

15. The improved strain of claim 14 in which said strain displays resistance to at least one of said analogs when the analog is present in a concentration of about 0.1 to about 1.0 mg/ml for serine hydroxamate or methionine hydroxamate or about 0.01 to about 0.8 mg/ml for glycine hydroxamate.

16. The improved strain of claim 15 in which said strain is resistant to all three analogs.

17. The improved strain of claim 14 which is selected from the group comprising *Corynebacterium glycinophilum* ATCC No. 39495 and *Corynebacterium glycinophilum* ATCC No. 39496.

* * * * *